United States Patent [19]

Lange et al.

[11] Patent Number: 4,889,554
[45] Date of Patent: Dec. 26, 1989

[54] DIPHENYL ETHER DERIVATIVES, THEIR PREPARATION AND THEIR USE FOR CONTROLLING UNDESIRABLE PLANT GROWTH

[75] Inventors: Arno Lange, Bad Duerkheim-Hardenburg; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 266,239

[22] Filed: Oct. 28, 1988

Related U.S. Application Data

[63] Continuation of Ser. No. 919,066, Oct. 15, 1986, abandoned.

[30] Foreign Application Priority Data

Oct. 15, 1985 [DE] Fed. Rep. of Germany ....... 3536664

[51] Int. Cl.⁴ .................. A01N 37/18; C07C 125/08
[52] U.S. Cl. ........................................ 71/118; 564/105
[58] Field of Search .......................... 564/105; 560/21; 71/107, 118

[56] References Cited

U.S. PATENT DOCUMENTS 3,564,607  2/1971  Breuer ............................... 564/105
3,928,416  12/1975  Bayer et al. .
4,400,530  8/1983  Grove ................................ 560/21
4,640,703  2/1987  Bohner et al. ..................... 564/105

FOREIGN PATENT DOCUMENTS 00200052  12/1980  European Pat. Off. .
0027837   5/1981   European Pat. Off. .
0019388   3/1983   European Pat. Off. .
48129     8/1975   Japan .

*Primary Examiner*—Alan Siegel
*Attorney, Agent, or Firm*—Keil & Weinkauf

[57] ABSTRACT

Diphenyl ether derivatives of the formula

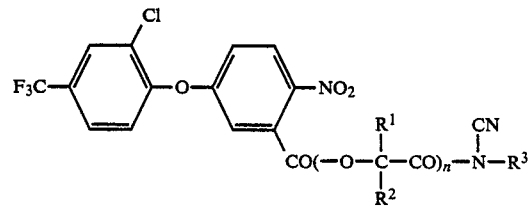

where $R^1$, $R^2$, $R^3$ and n have the meanings stated in the description, processes for their preparation, herbicides which contain these compounds as active ingredients, and a method of controlling undesirable plant growth by means of the novel compounds.

8 Claims, No Drawings

DIPHENYL ETHER DERIVATIVES, THEIR PREPARATION AND THEIR USE FOR CONTROLLING UNDESIRABLE PLANT GROWTH

This application is a continuation of application Ser. No. 919,066, filed on Oct. 15, 1986, abandoned.

The present invention relates to novel diphenyl ether derivatives, processes for their preparation, herbicides which contain these compounds as active ingredients, and a method of controlling undesirable plant growth by means of the novel compounds.

It is known that phenoxyphenylcarboxamides and compounds of the formula I in which —N(CN)— is replaced by oxygen or sulfur and $R^1$ and $R^2$ are each hydrogen or $C_1$–$C_4$-alkyl, -oxoalkyl or -hydroxyalkyl possess herbicidal activity (JP-A-48 129/1975, EP-A-19 388, EP-A-20 052, EP-A-27 837, U.S. Pat. No. 3,928,416 and U.S. Pat. No. 4,400,530).

We have found that dipheyl ether derivatives of the formula I

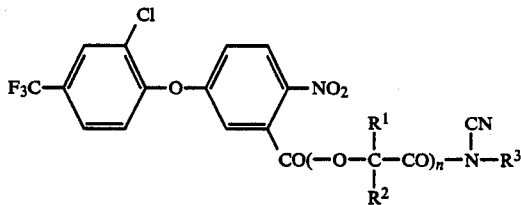

(I)

where $R^1$ is hydrogen, $C_1$–$C_4$-alkyl or $C_2$–$C_8$-alkoxyalkyl, $R^2$ is hydrogen, $C_1$–$C_4$-alkyol, $C_2$–$C_4$-alkenyl or $C_2$–$C_4$-alkynyl, $R^3$ is hydrogen, $C_1$–$C_4$-alkyl, $C_2$–$C_4$-alkenyl, $C_2$–$C_4$-alkynyl or $C_3$–$C_8$-cycloalkyl, each of these radicals being unsubstituted or substituted by $C_1$–$C_4$-alkoxy, and n is 0 or 1, and salts of the compounds in which $R^3$ is hydrogen, possess herbicidal activity and are selective with respect to crops.

Where the compounds of the formula I possess one or more asymmetric carbon atoms, they can occur in enantiomeric or diastereomeric forms, all of which are embraced by the claim.

In formula I, $R^1$ is hydrogen, $C_1$–$C_4$-alkyl, eg. methyl, ethyl, propyl, isopropyl, n-butyl, but-2-yl, isobutyl or tert-butyl, or alkoxyalkyl of 2 to 8 carbon atoms in total, eg. methoxymethyl, ethoxymethyl, 2-methoxyethyl, 2-ethoxyethyl, 1-methoxyprop-2-yl, 2-methoxypropyl, 4-methoxybutyl, 4-butoxybutyl, 6-methoxyhexyl or 6-ethoxyhexyl, $R^2$ is hydrogen, $C_1$–$C_4$-alkyl, eg. methyl, ethyl, propyl, isopropyl, n-butyl, but-2-yl, isobutyl or tert-butyl, $C_2$–$C_4$-alkenyl, eg. vinyl, prop-1-en-3-yl, prop-1-en-2-yl, prop-1-en-1-yl, but-1-en-1-yl, but-1-en-2-yl, but-1-en-3-yl or 2-methylprop-1-en-3-yl, or $C_2$–$C_4$-alkynyl, eg. ethynyl, propargyl or but-1-yn-1-yl, and $R^3$ is hydrogen, $C_1$–$C_4$-alkyl, $C_2$–$C_4$-alkenyl, $C_2$–$C_4$-alkynyl or $C_3$–$C_8$-cycloalkyl, and each of these radicals may be substituted by $C_1$–$C_4$-alkoxy, eg. methyl, ethyl, propyl, isopropyl, butyl, isobutyl, 2-methoxyethyl, 4-ethoxybutyl, vinyl, prop-1-en-3-yl, prop-1-en-1-yl, but-1-en-1-yl, 2-methylprop-1-en-3-yl, 4-ethoxy-but-1-en-1-yl, ethynyl, propargyl, but-1-yn-1-yl, cyclopropyl, cyclobutyl, cyclopentyl, cyclohexyl, cycloheptyl, cyclooctyl, 3-methoxycyclopentyl or 4-ethoxycyclohexyl.

Compounds in which $R^3$ in formula I is hydrogen can also occur as salts. Suitable salts are those which can be used in agriculture, for example alkali metal salts, in particular potassium or sodium salts alkaline earth metal salts, in particular calcium, magnesium or barium salts, manganese, copper, zinc and iron salts and, where Y is O or S, ammonium, phosphonium, sulfonium and sulfoxonium salts, eg. ammonium, trialkylammonium, tetraalkylammonium, benzyltrialkylammonium, trialkylsulfonium or trialkylsulfoxonium salts.

Preferred compounds are those in which $R^1$ and $R^2$ independently of one another are each hydrogen or methyl and $R^3$ is hydrogen or $C_1$–$C_4$-alkyl.

The diphenyl ether derivatives of the formula I can be obtained by reacting an acid derivative of the formula II

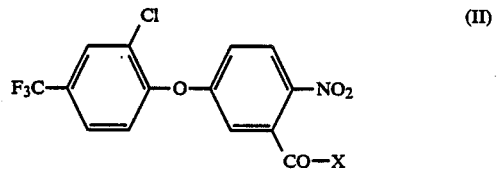

(II)

where X is halogen, preferably chlorine or bromine, or $C_1$–$C_4$-alkoxy, with a compound of the formula III

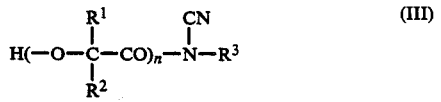

(III)

where $R^1$, $R^2$ and $R^3$ and n each have the above meanings.

The reaction is advantageously carried out in an inert diluent at from −40° to +150° C., preferably from −20° to +30° C., in the presence or absence of a base. The molar ratio of the acid derivative II to the compound III should be from 1:1 to 1:2, preferably from 1:1 to 1:1.2.

The compound III is preferably used in the form of a salt, in particular a metal salt of group 1A or 2A of the Periodic Table, or, where n is 1, an ammonium salt which may or may not be alkylated. For this purpose, an appropriate base is added to compound III. Examples of suitable bases are carbonates, bicarbonates, alcoholates, hydroxides, oxides and hydrides of alkali metals and alkaline earth metals, in particular of sodium, potassium, magnesium and calcium. Assuming the above preconditions, it is also possible to use organic bases, such as pyridine or tertiary amines.

In some cases, it is advisable to use the base in excess (based on compound III) and to carry out the conversion of the acid derivative II under base catalysis.

Examples of suitable inert diluents are water, aromatic and aliphatic hydrocarbons, such as naphtha, gasoline, benzene, toluene, xylene, pentane, hexane, cyclohexane or petroleum ether, aromatic and aliphatic halohydrocarbons, such as methylene chloride, chloroform, carbon tetrachloride, 1,1- and 1,2-dichloroethane, 1,1,1- and 1,1,2-trichloroethane, chlorobenzene, o-, m- and p-dichlorobenzene or o-, m- and p-chlorotoluene, aromatic and aliphatic nitrohydrocarbons, such as nitrobenzene, o-, m- and p-nitrotoluene or nitroethane, nitriles, such as acetonitrile, butyronitrile or isobutyronitrile, ethers, such as diethyl ether, di-n-propyl ether, tetrahydrofuran or dioxane, esters, such as ethyl acetoacetate, ethyl acetate or isobutyl acetate, ketones, such as acetone, methyl ethyl ketone, methyl isopropyl ketone or methyl isobutyl ketone, alcohols, such as methanol, ethanol or propanol, amides, such as N-methylformamide or N,N-dimethylformamide, and sulfur-containing solvents, such as dimethyl sulfoxide or sulfolane. Mixtures of these solvents may also be used.

The reaction is generally complete after from 0.5 to 5 hours. The end product can be isolated after separating off the inorganic salts and removing the diluent under reduced pressure. If necessary, products which are obtained in the solid state can be further purified by recrystallization. Products which are obtained in the form of an oil are further purified, if necessary, by means of column chromatography.

Where water or a water-miscible diluent is used, the reaction mixture may be introduced into water and, if necessary, neutralized. During this process, the end products are obtained in the solid state or as an oil. They are separated off and, if necessary, further purified as described above.

Similar preparation processes are known per se and are described in DE-A-1 907 193, DE-A-2 757 586 and Chem. Pharm. Bull. 24 (1976), 26. the starting materials used are known.

Diphenyl ether derivatives of the formula I where n is 1 may furthermore be obtained by reacting an acid derivative of the formula IV

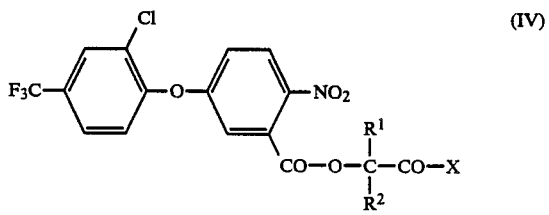

where R¹, R² and X have the above meanings, with a compound of the formula V

where R³ has the above meanings and A is hydrogen or a metal of group 1A or 2A of the Periodic Table, eg. lithium, sodium, potassium, magnesium or calcium.

Another possible method of preparing the diphenyl ether derivatives of the formula I (where n is 1) is to react an acid derivative of the formula VI

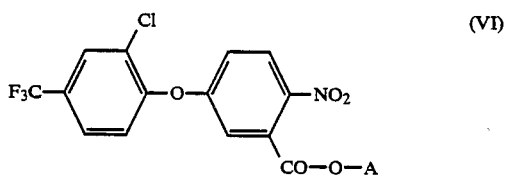

where A has the above meanings, with a halogen compound of the formula VII

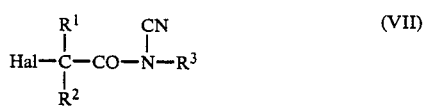

where R¹, R² and R³ have the above meanings and Hal is halogen, preferably chlorine or bromine.

The two last-mentioned methods of preparation are carried out at from −20° to +150° C., preferably from 30° to 120° C., but otherwise under the reaction conditions stated above (for the reaction II+III→I).

In this case too, the starting materials are known or can be prepared by a conventional method (eg. EP-A-148 119).

Finally, the diphenyl ether derivatives of the formula I, where R³ is hydrogen, may also be converted to the relevant N-substituted products by a conventional N-alkylation reaction.

The Examples which follow illustrate the invention.

EXAMPLE 1

(A) 51.4 g of n-propylamine in 300 ml of ether were initially taken, and 46 g of cyanogen bromide, dissolved in 100 ml of ether, were added dropwise at −10° C.

The mixture was stirred for a further hour at −10° C. and warmed up to room temperature in the course of 1 hour, and stirring was continued for a further 30 minutes at this temperature.

The mixture was filtered under suction, the residue was washed with ether and the ether solutions were evaporated down to give 35.5 g of n-propylcyanamide in the form of an oil.

(B) 1.68 g of n-propylcyanamide in 100 ml of absolute ether were initially taken, and 0.6 g of 80% strength by weight NaH was added at −20° C. in three portions. 7.4 g of 2-nitro-5-(2-chloro-4-trifluoromethylphenoxy)-benzoyl chloride in 20 ml of absolute ether were added dropwise at −20° C., the reaction mixture was warmed up to room temperature and stirring was continued overnight. The mixture was filtered, and the ether solution was washed 4 times with water, dried and evaporated down in a rotary evaporator to give 6.5 g of N-[2-nitro-5-(2-chloro-4-trifluoromethylphenoxy)-benzyl]-N'-propylcyanamide in the form of an oil, which solidified. The compound was stirred thoroughly with a small amount of 80% strength by weight aqueous methanol to give a product of melting point 90°–92° C. (compound No. 8).

EXAMPLE 2

4.08 g of methyl vinylglycolate in 80 ml of ether were initially taken with 3.2 g of pyridine. 11.4 g of 2-nitro-5-(2-chloro-4-trifluoromethylphenoxy)-benzoyl chloride, dissolved in 30 ml of ether, were added dropwise, and the mixture was stirred for a further hour. The precipitate was then filtered off and the filtrate was washed 4 times with water, dried, and evaporated down under reduced pressue in a rotary evaporator to give 12.7 g of an oil (compound No. 46).

NMR: 3.8 ppm, singlet, 33 protons; 5.4 ppm, doublet, 1 proton; 5.6 ppm doublet, 1 proton; 5.7 ppm, doublet, 1 proton; 6 ppm, 1 proton, multiplet 7.0 ppm, 7.2 ppm, 7.3 ppm, 7.6 ppm, 7.8 ppm, 8.1 ppm: 1 proton each with fine structure.

EXAMPLE 3

10 g of 2-nitro-5-(2-chloro-4-trifluoromethylphenoxy)-benzoic acid were dissolved in 20 ml of dimethyl sulfoxide, and 5 g of $K_2CO_3$ were added. The mixture was heated to 60° C. and then cooled to room temperature. Thereafter, 12.7 g of N-(2-bromopropionyl)-N-propylcyanamide were added dropwise, an exothermic reaction (to 29° C.) taking place. The mixture was stirred for a further hour and then stirred into 500 ml of water and extracted twice with ether. The ether phases were washed with water, dried and evaporated down. The residue was stirred thoroughly with 200 ml of cyclohexane, and the oil was separated off. It was freed from adhering cyclohexane under reduced pressure (1 mbar) to give 10 g of an oil (compound No. 36).

NMR: 0.9 ppm, triplet, 3 protons; 1.55 ppm, doublet, 3 protons, 1.6 ppm, multiplet, 2 protons; 3.5 ppm, triplet, 2 protons; 5.65 ppm, quartet, 1 proton; 6.9–8 ppm, multiplet, 6 protons.

The compounds below can be prepared by one of the methods described in Examples 1 to 3.

butanol, cyclohexanol, cyclohexanone, chlorobenzene, isophorone, and strongly polar solvents such as N,N-dimethylformamide, dimethyl sulfoxide, N-methylpyrrolidone and water, are suitable.

Aqueous formulations may be prepared from emulsion concentrates, dispersions, pastes, wettable powders or water-dispersible granules by adding water. To prepare emulsions, pastes and oil dispersions the ingredients as such or dissolved in an oil or solvent may be homogenized in water by means of wetting or dispersing agents, adhesives or emulsifiers. Concentrates which are suitable for dilution with water may be prepared from active ingredient, wetting agent, adhesives, emulsifying or dispersing agent and possibly solvent or oil.

TABLE 1

| Compound | $R^1$ | $R^2$ | $R^3$ | n | M.p. [°C.] |
|---|---|---|---|---|---|
| 1 | — | — | H | 0 | 95–116 |
| 2 | — | — | Na | 0 | |
| 3 | — | — | K | 0 | |
| 4 | — | — | Li | 0 | |
| 5 | — | — | $NH_4$ | 0 | |
| 6 | — | — | $CH_3$ | 0 | |
| 7 | — | — | $C_2H_5$ | 0 | 76–83 |
| 8 | — | — | $n-C_3H_7$ | 0 | 90–92 |
| 9 | — | — | $n-C_4H_9$ | 0 | 91–95 |
| 10 | — | — | $CH{\equiv}C-CH_2-$ | 0 | |
| 11 | — | — | $CH_3-O-C_2H_4-$ | 0 | 89–96 |
| 12 | — | — | ▷— | 0 | |
| 13 | — | — | $CH_2{=}CH-CH_2-$ | 0 | 82.5–86.5 |
| 14 | H | H | H | 1 | |
| 15 | H | H | Na | 1 | |
| 16 | H | H | $CH_3$ | 1 | |
| 17 | H | H | $n-C_3H_7$ | 1 | |
| 18 | $CH_3$ | H | H | 1 | |
| 19 | $C_2H_5$ | H | H | 1 | |
| 20 | $n-C_4H_9$ | H | H | 1 | |
| 21 | $CH_3$ | $CH_3$ | H | 1 | |
| 22 | $CH_3$ | $CH_2{=}CH-$ | H | 1 | |
| 23 | H | $CH_2{=}CH-CH_2-$ | H | 1 | |
| 24 | $CH_3-O-CH_2-$ | $CH_3$ | H | 1 | |
| 25 | H | $CH_2{=}CH-$ | H | 1 | |
| 26 | $CH_3-O-CH_2-$ | H | H | 1 | |
| 27 | $CH_3-O-C_2H_4-$ | $CH_3$ | H | 1 | |
| 28 | $CH_3-O-CH(CH_3)-CH_2-$ | $CH_3$ | H | 1 | |
| 29 | $CH_3-O-CH(CH_3)-CH_2$ | H | H | 1 | |
| 30 | H | H | $CH_3$ | 1 | |
| 31 | H | H | $C_2H_5$ | 1 | |
| 32 | H | H | $n-C_3H_7$ | 1 | |
| 33 | H | H | $n-C_4H_9$ | 1 | |
| 34 | $CH_3$ | H | $CH_3$ | 1 | |
| 35 | $CH_3$ | H | $C_2H_5$ | 1 | |
| 36 | $CH_3$ | H | $C_3H_7$ | 1 | Oil |
| 37 | $CH_3$ | H | $C_4H_9$ | 1 | |
| 38 | $C_2H_5$ | H | $CH_3$ | 1 | |
| 39 | $CH_3$ | $CH_3$ | $CH_3$ | 1 | |

The diphenyl ether derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as as kerosene or diesel oil, further coal-tar oils, and oils of vegetable and animal origin, aliphatic, cyclic and aromatic hydrocarbons such as toluene, xylene, paraffin, tetrahydronaphthalene, alkylated naphthalenes and their derivatives such as methanol, ethanol, propanol, Examples of surfactants are: alkali metal, alkaline earth metal and ammonium salts of ligninsulfonic acid, naphthalenesulfonic acids, phenolsulfonic acids, alkylarylsulfonates, alkylsulfates, and alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylpheol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycolether acetate, sorbitol esters, lignin sulfite waste liquors and methyl cellulose.

Powders, dusts and broadcasting agents may be prepared by mixing or grinding the active ingredients together with a solid carrier.

Granules, eg. coated, impregnated or homogeneous granules, may be prepared by bonding the active ingredients to solid carriers. Examples of solid carriers are mineral earths such as silicic acids, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood floor and nutshell meal, cellulosic powders, etc.

The formulations contain from 0.1 to 95, and preferably from 0.5 to 90, % by weight of active ingredient. The active ingredients may be applied pre- or (preferably) postemergence. If certain crop plants tolerate the active ingredients less well, application techniques may be used in which the herbicidal agents are sprayed from suitable equipment in such a manner that the leaves of sensitive crop plants are if possible not touched and the agents reach the soil or the leaves of the unwanted plants growing beneath the crop plants (post-directed, lay-by treatment).

To increase the spectrum of action and to achieve synergistic effects, the diphenyl ether derivatives of the formula I and their salts may be mixed and applied together with numerous representatives of othr herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, cyclohexane-1,3-dione derivatives, diphenyl ether derivatives of different structure, etc.

It may also be useful to apply the compounds of the formula I, either alone or in combination with other herbicides, or in admixture with other crop protection agents, eg. agents for combating pests or phytopathogenic fungi or bacteria. The compounds may also be mixed with solutions of mineral salts used to remedy nutritional or trace element deficiencies.

The amount of active ingredient applied depends on the time of year, the plants to be combated and their growth stage, and varies from 0.005 to 5 kg/ha, but is preferably from 0.01 to 1 kg/ha.

The herbicidal action of the diphenyl ether derivatives of the formula I on the growth of test plants is illustrated by the greenhouse experiments described below.

The vessels employed were plastic flower pots having a volume of 300 cm³ and filled with a sandy loam containing about 3% humus as the substrate. In the case of soybeans and groundnuts, peat was added to give a better stand. The seeds of the test plants were sown separately according to species.

For the postemergence treatment, the plants were first grown to a height of from 3 to 15 cm, depending on growth form, before being treted with the preparations of active ingredients which were suspended or emulsified in water and sprayed through finely distributing nozzles. For this treatment, either plants sown directly in the pots and grown there were selected, or plants grown from seedlings and transplanted. The application rates varied from active ingredient to active ingredient, and were 0.015, 0.03 and 0.06 kg/ha.

The pots were set up in the greenhouse, warmth-loving species in warmer areas at from 20° to 36° C., and species from moderate climates in areas at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The following plant species were used for the experiments.

| Abbreviation | Scientific name | Common name |
| --- | --- | --- |
| ABUTH | Abutilon theophr. | velvet leaf |
| AMARE | Amaranthus retoflexus | redroot pigweed |
| CHEAC | Chenopodium album | lambsquarters (goosefoot) |
| DATST | Datura stramonium | Jimsonweed, Florida beggarweed |
| EPHSS | Euphorbia spp. | member of the spurge family |
| GALAP | Galium aparine | catchweed bedstraw |
| LAMAM | Lamium amplexicaule | henbit |
| POLPE | Polygonum persicaria | ladysthumb |
| SEBEX | Sesbania exaltata | hemp sesbania (coffeeweed) |
| SOLNI | Solanum nigrum | black nightshade |
| TRZAW | Triticum aestivum | wheat |

The following active ingredients were used for comparison purposes:

| | YR³ | |
| --- | --- | --- |
| A | NH(CH₃) | EP 27, 837, Tab. I, comp. 2 |
| B | N(C₂H₅)₂ | EP 27, 837, Tab. I, comp. 5 |
| C | NH(C₂H₅) | EP 27, 837, Tab. I, comp. 3 |

On postemergence application of small amounts of active ingredients, a broad spectrum of unwanted plants was readily controlled in the greenhouse, for example with compound 35.

For combating unwanted broadleaved vegetation by the postemergence method, active ingredient 6 was far better suited than comparative agent A.

Common weed species were well controlled in the greenhouse by postemergence application of 0.06 kg/ha of active ingredients 7 and 8, without any appreciable damage being caused to wheat as the crop. Comparative agents B and C are far inferior to the novel compounds in their herbicidal action.

Unwanted broadleaved plants were selectively controlled on postemergence application in the greenhouse of 0.015 kg/ha of active ingredients 7 and 9, without any permanent damage being caused to groundnut plants. The herbicidal action of comparative agents B and C was unsatisfactory.

In view of the number of weeds which can be combated, the tolerance of the novel compounds by crop plants or the desired influence on growth, and in view of the numerous application methods possible, the compounds according to the invention may be used in a large number of crops; examples are given below:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |

-continued

| Botanical name | Common name |
|---|---|
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | corgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel diphenyl ether derivatives may be mixed and applied together with numerous representatives of other herbicidal or growth-regulating active ingredient groups. Examples of suitable mixture components are diazines, 4H-3,1-benzoxazine derivatives, benzothiadiazones, thiolcarbamates, halocarboxylic acids, triazines, amides, ureas, other diphenyl ethers, triazinones, uracils, benzofuran derivatives, cyclohexane-1,3-dione derivatives, etc.

It may also be useful to apply the compounds of the formula I, either alone or in combination with other herbicides, in admixture with other crop protection agents, eg. agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A diphenyl ether of the formula

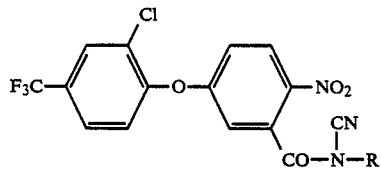

where R is hydroen or an unsubstituted or $C_1$–$C_4$-alkoxy substituted $C_1$–$C_4$-alkyl, $C_2$–$C_4$-alkenyl, $C_2$–$C_4$-alkynyl or $C_3$–$C_8$-cycloalkyl radical and salts of the diphenyl ether in which R is hydrogen.

2. The diphenyl ether of claim 1 in which R is hydrogen or $C_1$–$C_4$-alkyl.

3. The diphenyl ether of claim 1 in which R is methyl.

4. The diphenyl ether of claim 1 in which R is ethyl.

5. The diphenyl ether of claim 1 in which R is n-propyl.

6. The diphenyl ether of claim 1 in which R is n-butyl.

7. A herbicide comprising inert additives and an effective amount of the diphenyl ether of claim 1 or a salt thereof.

8. A method of controlling undesirable plant growth comprising treating undesirable plants and/or areas to be kept free of undesirable plants with a herbicidal amount of the diphenyl ether of claim 1 or a salt thereof.

* * * * *